United States Patent [19]

Baisch et al.

[11] Patent Number: 4,727,032

[45] Date of Patent: Feb. 23, 1988

[54] PROCESS FOR THE THERMOSTATIC CONTROL OF A SAMPLE FLUID TO BE ANALYZED, APPARATUS FOR PERFORMING THE PROCESS

[75] Inventors: Manfred Baisch; Horst Rüsbüldt; Manfred Knaus, all of Hamburg, Fed. Rep. of Germany

[73] Assignee: Eppendorf Geratebau Netheler & Hinz GmbH, Hamburg, Fed. Rep. of Germany

[21] Appl. No.: 702,252

[22] Filed: Feb. 15, 1985

[30] Foreign Application Priority Data

Feb. 15, 1984 [DE] Fed. Rep. of Germany ....... 3405293

[51] Int. Cl.⁴ .............................................. G01N 35/04
[52] U.S. Cl. ..................................... 436/47; 141/130; 219/521; 219/528; 422/65
[58] Field of Search ................. 422/65, 67, 102, 104; 141/130; 356/246; 436/47; 219/535, 521, 242

[56] References Cited

U.S. PATENT DOCUMENTS

| | | | |
|---|---|---|---|
| 1,704,413 | 3/1929 | Wait | 219/535 |
| 3,645,690 | 2/1972 | Rochte et al. | 422/67 |
| 3,746,837 | 7/1973 | Frey et al. | 219/521 |
| 3,753,657 | 8/1973 | Downing et al. | 141/130 |
| 3,770,382 | 11/1973 | Carter et al. | 422/65 |
| 3,832,140 | 8/1974 | Lorch et al. | 422/65 |
| 3,897,216 | 7/1975 | Jones | 422/65 |
| 3,905,772 | 9/1975 | Hartnett et al. | 422/102 |
| 3,951,605 | 4/1976 | Natelson | 422/65 |
| 4,168,955 | 9/1979 | Allington | 422/65 |
| 4,296,070 | 10/1981 | Montalto et al. | 422/64 |
| 4,459,265 | 7/1984 | Berglund | 422/65 |

Primary Examiner—Barry S. Richman
Assistant Examiner—C. M. Delahunty
Attorney, Agent, or Firm—Lane & Aitken

[57] ABSTRACT

A process for the purpose of the thermostatic control of a sample fluid to be analyzed, as well as reagents and optionally the solvents necessary for performing analyses in an automatically functioning analyzer, wherein the sample container containing the sample fluid as well as the cells containing the reagents are placed in a rack made from good thermally conducting material. The rack is fixed in the analyzer at the individual processing stations between two side walls. At least one of the side walls is heated, so that the rack is thermostatically controlled and, consequently, so is the sample fluid and the reagents.

11 Claims, 1 Drawing Figure

PROCESS FOR THE THERMOSTATIC CONTROL OF A SAMPLE FLUID TO BE ANALYZED, APPARATUS FOR PERFORMING THE PROCESS

BACKGROUND OF THE INVENTION

1. Field of the Invention

This invention relates to a process for the thermostatic control of a sample fluid to be analyzed, as well as of reagents and of optionally necessary solvents for performing analyses in an automatic analyzer, in which the associated samples and reagents are moved to different processing stations.

2. Description of the Prior Art

In many analyses and particularly in certain analyses in clinical laboratories and the like, it is of decisive importance that the analyses be performed at a specific, reproducible temperature, so that the analytical results obtained provide valid information and can be compared with other analytical results. This is particularly important in the case of enzyme-kinetic measurements and the like, in which the reaction process is determined during the analysis, said reaction process being very dependent on the temperature.

In a known analyzer marketed by Du Pont de Nemours (Deutschland) GmbH under the tradename "aca SYSTEM", different clinical analyses are performed on a sample fluid taken from a patient. A reagent container with the corresponding reagents is selected for each of the analyses to be performed. This reagent container comprises a plastic bag, which has various closed reception areas for reagents and a flexible cuvette or cell area. The bag is hung on a hook, which carries a code identifying the reagent contained in the bag. Part of the sample fluid is introduced into a sample container with which is associated a card identifying the patient. The sample container including the card, and the reagent container are then introduced into the analyzer and the analytical process is started. For this purpose, the sample fluid from the sample container, together with reagent and optionally solvent, are brought into the vicinity of the flexible cell in the analyzer and the reaction process which occurs is photometrically measured.

In order to be able to perform a correct analysis in this analyzer, the sample, the reagents in the reagent container and the optionally necessary solvent must be at a predetermined temperature prior to combining, and must be kept at this temperature during the analytical process. This is relatively simple with respect to the solvent, because it is stored in a container in the analyzer, which can be kept without difficulty at a constant temperature. However, the sample fluid and the reagents must initially be thermostatically controlled after being introduced into the analyzer, for which purpose they are brought into an area at a corresponding temperature and are kept there until they have reached this temperature. After combining the sample fluid, reagents and optionally the solvent, it must also be ensured that there is no change to the mixture temperature, i.e., in the area of the analyzer in which the photometric measurement of the analytical process takes place, the given temperature must be maintained.

It is immediately apparent that considerable expenditures for apparatus are required to provide large spaces in an analyzer which must be continuously kept at a constant temperature, and the problem of the present invention is therefore to simplify the thermostatic control of a sample fluid to be analyzed, together with reagents and optionally necessary solvents, together with the actual thermostatic control during the analytical process.

SUMMARY OF THE INVENTION

According to the invention, this problem is solved in conjunction with a process of the aforementioned type in that the sample container containing the sample fluid, together with the cells containing the reagents, are placed in a rack made from a good thermally conductive material, the rack is introduced into the analyzer and for delivery to the individual processing stations is moved in the direction of its longitudinal extension along a linear path, and, when stationary, the rack is fixed between two side walls extending parallel to the linear path, at least one of the side walls being heated.

Thus, in the process according to the invention use is made of a rack made from good thermally conductive material, such as metal and such as is e.g. described in related German patent application No. P 34 05 292.5 which corresponds to the simultaneously filed U.S. application of Manfred Baisch and Horst Rusbuldt, entitled "Process for Performing Sample Analyses and Rack for Performing the Process," Ser. No. 702,253, filed Feb. 15, 1985, which is hereby incorporated by reference. All the containers containing the sample fluid and reagents are placed in this rack and following insertion into the analyzer the rack is secured between two side walls, at least one and preferably both of which are heated. These heated side walls consequently give off heat to the rack so that the containers placed in the rack and consequently also their contents are heated relatively rapidly and simply to a temperature as required for the further processing sequence. During the further processing sequence, which initially essentially consists of introducing sample fluid into the various cells and the optionally necessary addition of solvents, the rack is reciprocated along the linear path and for each processing stage is again fixed between the side walls, so that in each rack-fixing position heat is transferred from the side walls to the rack and consequently a thermostatic control takes place. There is correspondingly also a thermostatic control during the photometric measurement of the analyses performed, so that there is also no disturbing temperature change during these analytical processes.

In order to bring the rack into a clearly defined spatial position at right angles to its longitudinal extension in the different fixing positions, it can be pressed by one transversely displaceable side wall against the other stationary side wall whereby the rack engages with a stationary side wall in each fixed position, so that the openings for receiving the different containers in the rack have the same distance from the stationary side wall in each fixed rack position.

The rack can be supported by projections provided on the side wall, so that during movement along the linear path it substantially slides on the projections and is always at the same height with respect to the side walls.

The invention also relates to an apparatus for performing the process according to the invention, which is characterized by two side walls laterally defining the linear path for the rack movement, whereby at least one is heatable and at least one is movable at right angles to the path. Preferably, one side wall is kept stationary.

According to a further embodiment of the apparatus according to the invention, the movable side wall is fixed to leaf spring-like fastenings and is connected to a thrust piece, which is fixed to a support movable between a rack-release position and a rack-fixing position. Thus, through the displacement of the support controlled by the analyzer, and by means of the thrust piece the corresponding displacement of the movable side wall can take place. The leaf spring-like fastenings permit a very simple assembly and easily compensate tolerances in the rack dimensions.

It is possible to provide, in the area between the movable side wall and the support, a slide that is movable parallel to the path and carries a conveying member for the positive engagement with the rack, together with a locking part. In the path direction, the support can carry spaced locking areas for the locking engagement with the locking part in the rack-fixing position of the support.

With the aid of such a slide and the conveying member fitted thereto, the rack can be moved in simple manner along the linear path and brought into the desired positions, whilst the engagement of the locking part and the locking area leads to a precise positioning of the rack at a point given by the particular locking area.

To ensure that the facing surfaces of the two side walls are not gradually worn by abrasion as a result of the movement of the rack along the linear path and to ensure that the facing surfaces of the side walls do not lead to corresponding abrasion phenomena on the outer faces of the rack, e.g. plastic guide rails running parallel to the path can be provided on the facing surfaces of the two side walls and these can be displaced into the walls counter to spring tension.

During the movement along the linear path, the guide rails made from a corresponding suitable material prevent an abrasioncausing engagement between the outer faces of the rack and the facing surfaces of the two side walls, whilst they are pressed into the latter in the rack-fixing position, so that there is a surface contact between the lateral faces of the rack and the facing surfaces of the two side walls and consequently a good heat transfer.

According to a particularly advantageous embodiment, there are two guide rails in each side wall wherein each lower guide rail has a web projecting into the space between the side walls for supporting the rack in its release position. Thus, there is no need for additional projections for supporting the rack during its movement along the linear path between the two side walls and said support function is assumed by the lower guide rails. There is sufficient space between the webs of the two side walls to enable the conveying member to positively engage with the rack between the same.

DESCRIPTION OF THE PREFERRED EMBODIMENTS

Figure 1:
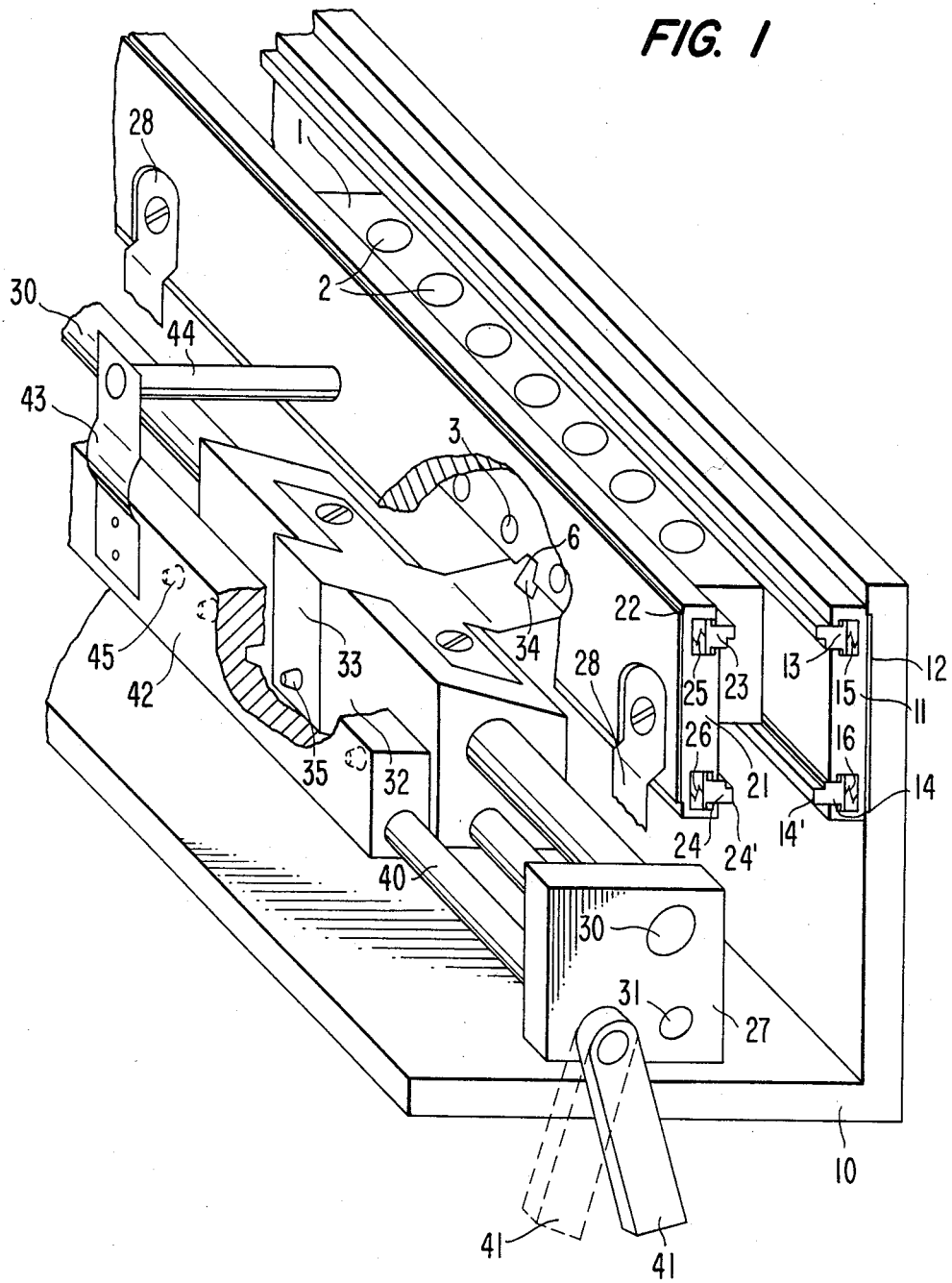
FIG. 1 is a perspective view of an apparatus suitable for use in the present invention

The invention is described in greater detail hereinafter relative to FIG. 1, which shows the apparatus according to the invention.

The illustrated part of the apparatus is arranged on an assembly angle bracket 10 fixed in stationary manner in the casing of an analyzer. In the upper end area of one leg of the assembly bracket 10 is fixed a stationary side wall 11, which is made from good thermally conducting material, and a heater 12 is provided between side wall 11 and bracket 10 and enables said side wall to be heated in a controlled manner. Opposite stationary side wall 11 is provided a side wall 21, which is also made from a good thermally conducting material and which is fixed to the assembly bracket 10 in an illustrated manner by means of two leaf spring-like fastenings 28. A heater 22 for the controlled heating of side wall 21 is provided on the back surface, i.e. on the side of side wall 21 remote from side wall 11. The facing surfaces of side walls 11 and 21 in each case contain reception slots in which are arranged guide rails 13, 14 and 23, 24. Between the particular slot bottom and the guide rails are located springs 15, 16 and 25, 26, which force the guide rails 13, 14 and 23, 24 into the position shown in the drawing. The function and operation of the guide rails will be described hereinafter.

To the outside of side wall 21 is fixed a journal or pinlike thrust piece 44, whose free end is fitted into a spring strip 43 serving as a fastening. Spring strip 43 is fixed to an elongated and substantially rectangular support 42 by means of screws or rivets. The support is positioned on a stop shaft 40, which is mounted in bearing blocks 27, only one being shown in the drawing, fixed to assembly bracket 10, so as to rotate about the longitudinal axis thereof. To the represented outer end of the stop shaft 40 is attached an operating lever 41, which enables the stop shaft 40 to be rotated.

Adjacent to stop shaft 40 and closer to side wall 21 are provided two parallel guide rods 30, 31, which are fixed in non-rotatable manner in bearing blocks 27. A slide 32 is movably mounted on said guide rods in the longitudinal direction thereof, the drive of said slide not being shown. The drive can for example be constituted by a linear motor. To slide 32 is fixed a resilient mounting 33, which on one leg carries a cross-sectionally trapezoidal conveying member 34 and on an opposite leg a frustum-shaped locking part 35. In the still to be described rack-fixing position, the locking part 35 engages with correspondingly shaped locking recesses 45 in supports 42, so that in each case clearly defined positions of the slide 32 relative to the longitudinal direction of the guide rods 30, 31 are obtained. The conveying member 34 engages with a correspondingly shaped slot 6 in the bottom of the rack 1 located between side walls 11 and 21 (the separate representation in the drawing merely serves to illustrate the shapes).

The elongated rack 1 has a substantially rectangular cross-section and is made from a good thermally conducting material, such as metal. It has upwardly open reception openings 2 for a sample container and various cells or cuvettes containing reagents. These reception openings are shaped in such a way that the cells can only be inserted in rack 1 so that their optical faces to be transilluminated for measuring the reaction processes are located in the vicinity of bores 3 extending at right angles through rack 1, a bore 3 obviously being associated with each reception opening 2. It is pointed out in this connection that the photometric measurement station is not shown in the drawing and can in fact be located at a point outside the drawing plane and further to the rear. Obviously openings are provided in the side walls at this point in order to permit transillumination.

In order to carry out analyses, the rack 1, filled with the sample container and the cells, is placed in the analyzer and is moved between the two side walls 11, 21, which in the above-characterized position are at such a distance from one another that the rack 1 can be moved in the direction of its longitudinal extension. In this position, the edge areas of the base surface of rack 1 rest on webs 14' and 24' of guide rails 14, 24, whilst on the one hand guide rails 13 and 23 and on the other hand corresponding surfaces of the guide rails 14, 24 engage with the outer faces of rack 1 and guide same during displacement movements. The displacement movements result from the movement of slide 32 along guide rods 30, 31, slide 32 entraining rack 1 by means of the conveying member 34 which engages with slot 6. In said operating position of the apparatus, operating lever 41 is in the extended position i.e. pivoted to the right in the drawing, so that the area of support 42 located above stop shaft 40 is pivoted to the left. In this position, on the one hand thrust piece 44 has moved side wall 21 away from side wall 11 by a certain distance and on the other hand the locking recesses 45 are disengaged from the locking part 35, so that the movement of slide 32 along guide rods 30, 31 is not impeded by locking engagement.

As has already been mentioned, rack 1 is moved longitudinally by the displacement of slide 32. This movement is controlled in such a way that rack 1 is brought into a processing position, e.g. for introducing sample fluid into a cell containing a reagent, a position for introducing solvent into the cell, a position for the photometric measurement, etc. When such a position has been reached, the operating lever 41 is pivoted to the left into the position indicated by the broken line by means of an unillustrated drive. Thus, the part of support 42 located above stop shaft 40 is pivoted, so that the thrust piece 44 displaces side wall 21 in the direction of side wall 11. Thus, guide rails 13, 14, 23, 24 are pressed into the associated reception slots counter to the tension of springs 15, 16, 25, 26 and the rack 1 is fixed between the facing surfaces of the side walls 11 and 21. In this rack-fixing position, leaf spring 43 compensates the tolerances and consequently ensures the rack-locking position.

On passing from the above-characterized rack-release position into the rack-fixing position, there is a displacement of the rack 1 from the rack-release position toward side wall 11. This movement can take place despite the engagement of conveying member 34 with the rack slot 6, because member 34 and slot 6 are shaped in such a way that between them a relative movement at right angles to the longitudinal extension of rack 1 is possible.

When the part of support 42 located above stop shaft 40 is moved closer to slide 32 on passing into the rack-fixing position, a locking recess 45 engages with the locking part 35 fixed to slide 32. As the locking part 35 and locking recess 45 are constructed in frustum-shaped manner, this engagement leads to a certain displacement of slide 32 in the longitudinal direction of guide rods 30, 31, if locking recess 45 and locking part 35 are not precisely aligned with one another following the conveying movement of slide 32. This displacement movement brings about a correction of the position of slide 32, so that the exact rack position is given by the position of the locking recess 45 on the stationary support 42.

As has already been stated, the lateral faces of rack 1 in the rack-fixing position engage on the facing surfaces of side walls 11 and 21. As side walls 11, 21 are heated in a controlled manner by heaters 12, 22, there is a corresponding heat transfer to rack 1 and consequently a controlled heating of the sample fluid in the sample container as well as the reagents in the cells. This thermostatic control is repeated in each rack-fixing position, so that even after mixing has taken place and during photometric measurement, there is always a thermostatic control so that the temperature of the different substances is kept constant in a simple manner throughout the operation.

We claim:

1. A process for the thermostatic control of a sample fluid to be analyzed, as well as of at least reagents for performing analyses in an automatic analyzer in which at least corresponding samples and reagents are moved to different processing stations, comprising the steps of placing a sample container containing the sample fluid, together with at least one cell or cuvette containing at least one reagent in a rack made from a thermally conductive material, said rack defining a length; introducing said rack into said analyzer moving said rack in the direction of the length of said rack along a linear path between two side walls of said analyzer extending parallel to said linear path in order to successively deliver said rack to individual processing stations along the linear path within said analyzer; heating at least one of said side walls; holding said rack stationary at the individual processing stations; when said rack is held stationary, moving one of said side walls into engagement with said rack, said moving one of said sidewalls causing said rack to be pressed into engagment with the other of said side walls so that there is heat transfer between said rack and at least one of said side walls; and moving the previously moved side wall out of engagement with said rack prior to again moving said rack along said linear path.

2. A process for the thermostatic control of a sample fluid to be analyzed, as well as of at least reagents for performing analyses in an automatic analyzer in which at least corresponding samples and reagents are moved to different processing stations, comprising the steps of placing a sample container containing the sample fluid, together with at least one cell or cuvette containing at least one reagent in a rack made from a thermally conductive material, said rack defining a length; introducing said rack into said analyzer; moving said rack in the direction of the length of said rack along a linear path between two side walls of said analyzer extending parallel to said linear path in order to successively deliver said rack to individual processing stations along the linear path within said analyzer heating at least one of said side walls; holding said rack stationary at the individual processing stations; when said rack is held stationary, moving at least one of said side walls into engagement with said rack to fix said rack between said side walls, and to heat said rack and said sample fluid and said at least one reagent carried thereby; and moving said at least one movable side wall out of engagement with said rack prior to again moving said rack along said linear path.

3. The process according to claim 1, further comprising the step of supporting said rack in said linear path by means of projections disposed on said side walls.

4. The process according to claim 1, wherein the step of moving at least one of said side walls into engagement with said rack includes pressing said rack into engagement with the other of said side walls so that there is heat transfer between said rack and at least one of said side walls.

5. Apparatus for the thermostatic control of fluids to be analyzed in an analyzer having a plurality of processing stations along a linear path, comprising:
- a rack made from a thermally conductive material and constructed and arranged to hold a plurality of containers;
- a sample container for containing a sample fluid positioned in said rack;
- at least one reagent container for containing at least one reagent positioned in said rack;
- means for moving said rack along a linear path to successively deliver said rack to individual processing stations of an analyzer along the linear path;
- two side walls laterally defining the linear path along which said rack is moved, at least one of said side walls being movable;
- means for heating at least one of said side walls; and
- means for moving said at least one movable side wall from a disengaged position out of engagement with said rack to an engaged position in which said at least one movable side wall engaged said rack when said rack is positioned in said linear path so as to press said rack into engagement with the other of said side walls, whereby said rack and any samples or reagents carried thereby are heated by contact with the heated at least one of said side walls.

6. The apparatus according to claim 5, further comprising:
- guide rails extending parallel to said linear path, said guide rails being positioned in opposing surfaces of said two side walls;
- recesses in said side walls receiving said guide rails; and
- means for biasing said guide rails toward positions projecting beyond the opposing surfaces and into said linear path.

7. The apparatus according to claim 6 wherein said guide rails are made from plastic.

8. The apparatus according to claim 6, wherein said guide rails comprise an upper and a lower guide rail positioned in recesses in the surface of each of said side walls, each lower guide rail having a web portion extending into said linear path and being positioned and arranged to support said rack when said at least one movable side wall is in the disengaged position.

9. The apparatus according to claim 5, wherein one of said side walls if fixed and the other of said side walls is movable.

10. The apparatus according to claim 9, wherein said means for moving said at least one movable side wall comprises:
- a movable support;
- means for supporting said movable side wall, said supporting means including a plurality of leaf springs;
- and means for connecting said support to said movable side wall for movement with said movable side wall, said connecting means including a thrust piece, said movable support being movable between a position in which said movable side wall releases said rack for movement and a position in which said movable side wall fixes said rack.

11. The apparatus according to claim 10, wherein said means for moving said rack comprises:
- a slide movable parallel to said linear path;
- means for positively engaging said slide with said rack; and
- means for releasably locking said slide with said support, said locking means comprising a plurality of spaced locking recesses in said support and a locking protrusion on said slide, said locking protrusion being receivable in any of said locking recesses; said means for releasably locking said slide being constructed and arranged so that when said movable side wall is in said engaged position, said locking protrusion is received within one of said locking recesses.

* * * * *

UNITED STATES PATENT AND TRADEMARK OFFICE
CERTIFICATE OF CORRECTION

PATENT NO. : 4,727,032

DATED : February 23, 1988

INVENTOR(S) : MANFRED BAISCH ET AL

It is certified that error appears in the above-identified patent and that said Letters Patent is hereby corrected as shown below:

Column 6, line 18, --;-- should be inserted after "analyzer",

Column 6, line 49, --;-- should be inserted after "analyzer",

Column 7, line 22, "engaged" should be --engages--; and

Column 8, line 9, "if" should be --is--.

Signed and Sealed this

Second Day of May, 1989

Attest:

Attesting Officer

DONALD J. QUIGG

Commissioner of Patents and Trademarks